United States Patent [19]

McManus

[11] Patent Number: 5,200,402

[45] Date of Patent: Apr. 6, 1993

[54] ANTI MICROBIAL MAFENIDE-PHOSPHANILATE COMPOUND, PHARMACEUTICAL COMPOSITIONS AND METHOD OF USE THEREFOR

[75] Inventor: Albert McManus, San Antonio, Tex.

[73] Assignee: U.S. Army Medical Research & Development Command, Fort Detrick, Frederick, Md.

[21] Appl. No.: 782,179

[22] Filed: Oct. 24, 1991

[51] Int. Cl.$^5$ .................. A61K 31/685; C07F 9/38
[52] U.S. Cl. ........................... 514/76; 562/11
[58] Field of Search ..................... 514/76; 562/11

[56] References Cited

U.S. PATENT DOCUMENTS

| | | | |
|---|---|---|---|
| 2,288,531 | 6/1942 | Klarer | 562/65 X |
| 3,497,599 | 2/1970 | Nachod | 514/603 |
| 3,694,447 | 9/1972 | Pagano | 546/105 |
| 3,794,723 | 2/1974 | Pagano | 514/114 |
| 4,125,610 | 11/1978 | Redl | 514/114 |
| 4,666,896 | 5/1987 | Warner et al. | 562/11 X |

*Primary Examiner*—Mary C. Lee
*Assistant Examiner*—Michael Ambrose
*Attorney, Agent, or Firm*—John Francis Moran; Werten F. W. Bellamy

[57] ABSTRACT

The present invention relates to a synergistic antimicrobial compound (mafenide-phosphanilate) having especially high activity for topical prophylaxis and therapy of burn wound infections. The invention further relates to anti-microbial pharmaceutical compositions and a method for treating microbial infection. More particularly, the invention relates to the effective unexpectedly improved treatment of burn wounds involving Pseudomonas and Proteus bacteria.

16 Claims, No Drawings

ANTI MICROBIAL MAFENIDE-PHOSPHANILATE COMPOUND, PHARMACEUTICAL COMPOSITIONS AND METHOD OF USE THEREFOR

Technical Field

The present invention relates to a synergistic antimicrobial compound (mafenide-phosphanilate) having especially high activity for topical prophylaxis and therapy of burn wound infections. More particularly, the invention relates to the effective treatment of burn wounds against Pseudomonas and Proteus bacteria.

BACKGROUND ART

Mafenide is a known anti-microbial agent active against strains of both gram (−) and gram (+) bacteria and some fungi. Its salts are known to have undesirable side effects.

The following described documents provide background information relating to mafenide compounds and phosphanate salts of other compounds.

U.S. Pat. No. 2,288,531 to Klarer relates to 4-aminomethyl-benzenesulphonamide which exhibits antibacterial properties. The Klarer patent specifically relates to the mafenide compound claims which was issued to Winthrop Chemical Company, Inc. in 1942.

U.S. Pat. No. 3,497,599 to Nachod relates to acid addition salts of para-aminomethyl benzene sulfonamide. The acid addition salts exemplified are acetic acid, propionic acid, citric acid, isocitric acid, CIS-aconitic acid, succinic acid, fumaric acid, malic acid and glutamic acid. There are no teachings of a phosphate acid of any kind in Nachod, particularly a phosphanilic acid. The preferred salt disclosed by Nachod is the acetate salt species.

U.S. Pat. No. 4,666,896, issued May 19, 1987 to Warner et al, relates to dinalidixate and diphosphanilate salts of chlorhexidine. Such compositions exhibit synergism as compared with comparable concentrations of chlorhexidine and the respective free acid. There is no teaching that phosphanilate salts of any other drug would indicate any synergism. Further, chlorhexidine is extraordinarily different in structure from mafenide. However, a mixture of phosphanilic acid, trimethoprin, neomycin and streptomycin has also been reported to show synergistic action but not as a salt.

The art has recognized that mafenide has serious drawbacks due to its toxicities of excess osmolality and carbonic anhydrase inhibitory activity. Further, the toxicities of mafenide are increased as the effective amount of mafenide is increased. Presently available mafenide compounds, including salts, all show such toxicities.

Accordingly, there has been a long standing need in the art for compositions having the effect of mafenide which avoid or reduce the excess osmolality and carbonic anhydrase inhibitory activity brought about as compared to mafenide. This need is particularly true in treatments that apply mafenide as an anti-microbial agent in the treatment of burn victims since such high concentrations of mafenide are required for effective anti-microbial activity.

DISCLOSURE OF THE INVENTION

An object of the present invention is to provide a compound having the anti-microbial effect of mafenide which either avoids or reduces the excess osmolality and carbonic anhydrase inhibitory activity brought about as compared to mafenide.

Another object of the present invention is to provide a pharmaceutical composition comprising a compound having the anti-microbial effects of mafenide which avoids or reduces the excess osmolality and carbonic anhydrase inhibitory activity brought about as compared to mafenide.

A still further object of the present invention is to provide an improved method for the treatment of microbial infections in a non-human mammal or a human being which comprises the administration of an effective amount of a compound according to the invention or a pharmaceutical composition having an effective amount of a compound according to the invention. The improved methods would provide the anti-microbial effects of mafenide and avoid or reduce the excess osmolality and carbonic anhydrase inhibitory activity brought about as compared to mafenide. More particularly, an improved method for the treatment of burn victims is provided which avoids the high concentrations of mafenide which are required for effective anti-microbial activity.

DESCRIPTION OF PREFERRED EMBODIMENTS

In accordance with this invention there are disclosed compounds of the formula

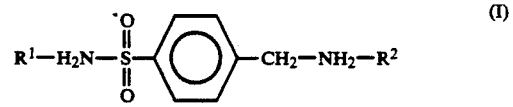

wherein $R_1$ and $R_2$ independently are absent or a phosphanilate group of formula II

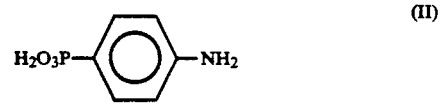

with the proviso that at least one of $R^1$ and $R^2$ is said phosphanilate group of formula II including isomeric and polymer forms.

Also, disclosed are pharmaceutical compositions comprising the compounds of the present invention for systemic or topical administration to humans and animals in the treatment of microbial infection.

Further disclosed is a method for treating or alleviating a microbial infection in a mammal which comprises administering to a mammal an anti-microbial effective amount of a compound according to the invention.

Surprisingly, the presently claimed mafenide phosphanilate compounds show significant therapeutic activities that are greater than the activities of the mafenide.

BEST MODE FOR CARRYING OUT THE INVENTION

In accordance with this invention there are disclosed compounds of the formula

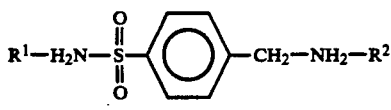

wherein $R^1$ and $R^2$ independently are absent or a phosphanilate group of formula II

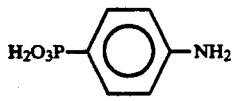

with the proviso that at least one of $R^1$ and $R^2$ is said phosphanilate group of formula II including isomeric forms.

Preferred are compounds according to Formula 1, wherein $R^1$ and $R^2$ are each a phosphanilate group of Formula II. Further preferred are compounds according to Formula I, wherein $R^2$ is a phosphanilate group of formula II and $R^1$ is absent.

Also, the compounds of the present invention are useful in pharmaceutical compositions for systemic or topical administration to humans and animals in unit dosage forms, such as tablets, capsules, pills, powders, granules, suppositories, sterile parenteral solutions or suspensions, sterile non-parenteral solutions or suspensions, oral solutions or suspensions, oil in water or water in oil emulsions and the like, containing suitable quantities of an active ingredient. Topical applications can be made in the form of ointments, creams, lotions, jellies, sprays, dusches and the like. For oral administration either solid or fluid unit dosage forms can be prepared with the compounds of Formula I. The compounds are useful in pharmaceutical compositions (wt %) of the active ingredient with a carrier or vehicle in the composition at about 1 to 20%, preferably about 1 to 10% and most preferably at about 2%.

Either fluid or solid unit dosage forms can be readily prepared for oral administration. For example the compounds of Formula I can be mixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. Capsules may be formulated by mixing the compounds with a pharmaceutical diluent which is inert and inserting this mixture into a hard gelatine capsule having the appropriate size. If soft capsules are desired, a slurry of the compound with an acceptable vegetable, light petroleum, or other inert oil can be encapsulated by machine using the gelatine capsule.

Suspensions, syrups and elixirs may be used for oral administration of fluid unit dosage forms. A fluid preparation including oil may be used for oil soluble forms. A vegetable oil such as corn oil, peanut or safflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener such as sugar, saccharin or a biological sweetener and a flavoring agent in the form of an elixir pharmaceutical preparations may be used having an acceptable sweetener such as sugar, saccharine or a biological sweetener and a flavoring agent in the form of an elixir. Pharmaceutical compositions for parenteral and suppository administration can also be obtained using techniques standard in the art.

Accordingly, the compound according to the invention are useful in a method for treating or alleviating a microbial infection in a mammal which comprises administering to a mammal an anti-microbial effective amount of a compound according to the invention.

A preferred use of the compounds according to the present invention is as topical anti-microbial agents suitable for application to a burned area in mammals, for example, the skin. Accordingly, compositions suitable for administration to these areas are particularly included within the invention. If a more concentrated slow release form is desired it may be administered. Accordingly, incorporation of the active ingredients in a slow release matrix may be implemented for administering topically. The compounds may be administered at about 1 to 20% of the composition and preferably about 1 to 10 wt % of the active ingredient in the vehicle or carrier. Even more preferred are compositions containing about 2 wt % of the active ingredient in the vehicle or carrier.

A transdermal therapeutic system when used are self contained-dosage forms that, when applied to intact skin, deliver drug(s) at a controlled rate to the systemic circulation or effected area. Advantages of using the transdermal rooting include enhanced therapeutic efficacy, reduction in the frequency of dosing, reduction of side effects due to optimization of the blood-concentration vs. time profile, increasing patient compliance due to elimination of multiple dosing schedules, bypassing the hepatic "first-pass" metabolism, avoiding gastrointestinal incompatibilities and providing a predictable and extended duration of activity. However, the main function of the skin is to act as a barrier to entering compounds. As a consequence, transdermal therapy is limited to drugs which possess the desirable physicochemical properties for diffusion across the skin barrier. One effective method of overcoming the barrier function of the skin is to include a penetration enhancer in the formulation of a transdermal therapeutic system. See Barry W.: *Dermatological Formulations: Percutaneous Absorption*, Dekker, N.Y. (1983); Bronough et al *Percutaneous Absorption, Mechanisms-Methodology Drug Delivery*. (Dekker, New York, N.Y., 1985); and Monkhouse et al, *Transtermal Drug Delivery Problems and Promises, Drug Dev. Ind. Pharm.*, 14, 183-209 (1988).

A penetration enhancer is a chemical compound that, when included in a formulation, temporarily increases the permeability of the skin to a drug which allows the drug to be absorbed in a shorter period of time. Several different types of penetration enhancers have been reported such as dimethylsulfoxide, n-decyl methyl sulfoxide, N,N-dimethylacetamide, N,N-dimethylforamide, 1-dodecylazacycloheptan-2-one (Azone), propylene glycol, ethanol, pyrrolidones such as N-methyl-2-pyrrolidone (NMP) and surfactants. See Bronough et al, supra, and Stroughton et al, Azone: A New Non-toxic Enhancer of Percutaneous Penetration, *Drug Dev. Ninc. Pharm.*, 9, 725-744 (1983).

The compounds according to the invention can be present in the reservoir alone or in combination form with pharmaceutical carriers. The pharmaceutical carrier acceptable for the purpose of this invention are the art known carriers that do not adversely effect the drug, the host, or the material comprising the drug delivery system. Suitable pharmaceutical carriers include sterile water; saline; dextrose; dextrose in water or saline; condensation products of caster oil and ethylene oxide combining about 30 to about 35 moles of ethylene oxide per mole of caster oil; liquid acid; lower alkenols; oil such as corn oil, peanut oil, sesame oil, and the like; with emulsifiers such as mono- or diglyceride of a fatty acid; or a phosphatide, e.g., lecithin, and the like; glycols; polyalkylene glycols; aqueous media in the presence of a suspending agent, for example, sodium carboxymethylcellulose; sodium alginate; poly(vinylpyrrolodine); and the like, alone or with suitable dispensing agents such as lecithin, polyoxethylene stearate; and the like. The carrier may also contain adjuvants such as preserving, stabilizing, wetting, emulsifying agents and the like together with the penetration enhancer as described above.

The effective dosage for mammals may vary due to such factors as age, weight, activity level or condition of the subject being treated. Typically, an effective dosage of a compound according to the present invention is about 10 to about 500 mg when administered by means other than topical application. Compounds of the present invention may be administered at about 1 to 20 wt % of the composition, and preferably at about 1 to 10 wt %.

Compounds according to the present invention are prepared by selective precipitation from the combination of water-soluble forms of mafenide and phosphanilic acid. For example, mafenide hydrochloride (or acetate) and phosphanilic acid (solubilized with aqueous sodium bicarbonate or alkali) are mixed in water at a mole ratio of 1:1 and the mafenide phosphanilate is recovered. Higher ratios of the phosphanilic acid can be added in order to produce a Di=2 phosphanilate salt according to the invention.

Also, even higher ratios of phosphanilic acid can be added to form polymeric chains of phosphanilic acid (the acid head or one phosphanilic acid residue can combine with the basic tail of another phosphanilic acid residue to form a polymeric chain) with a mafenide residue inserted between two phosphanilic acid residues.

The effectiveness of the presently claimed compounds which avoid or reduce the excess osmolality and carbonic anhydrase inhibitory activity as compared to the mafenide-hydrochloride and mafenide-acetate were compared. The experimental animal protection is as follows.

EXAMPLE I

As a background procedure, the experimental *Pseudomonas aeruginosa* Burn Wound Sepsis Models employed for Mafenide Phosphanilate evaluation were similar to the systems used by Lindberg and others (Ann. NY Acad. Sci. 150 (3); 950–960, 1968, and were used in the laboratory evaluation relating to mafenide hydrochloride salt and later mafenide acetate salt.

The experimental systems use laboratory rats with 20% full thickness scald wounds as susceptible hosts for fatal burn wound infections with pseudomonas aeruginosa (PA). Soon after scalding, anesthetized rats are inoculated on the wound surface with a suspension of virulent (PA) organisms and the animals are then placed in individual cages. If the animals are not further treated, mortality from PA invasive wound sepsis is greater than 90%.

Experimental topical therapies, e.g., mafenide phosphanilate can be evaluated for therapeutic activity by their ability to intercede in the infection process. Each experimental run would include several control groups. A group of animals with only burns (not infected) serves as a control for the burn itself which is normally not fatal.

As mentioned above, burned inoculated animals are expected to have greater than 90% mortality (this requires a separate burn infected burn control group to confirm the expected mortality). A group of burned inoculated animals treated with a known effective topical agent (therapy control) is also normally included to confirm that the induced infection is controllable.

The following data (presented in Table I below) are a summary of eight experiments using PA strain 59-12-4-4 and control (sulfamylon) and experimental (mafenide phosphanilate) therapies applied 24 hours after burning and inoculation. Mafenide acetate is also compared in this study to the mafenide phosphanilate, the infection control and the burn control. Treated animals were treated once per day for 10 days and mortality was recorded for 28 days after burning. Agent concentrations were the commercial 11.2% mafenide acetate cream and 2.0% mafenide phosphanilate made up in a cream base.

TABLE I

Therapeutic Activities of Mafenide Acetate (11.2%) and Mafenide-Phosphanilate (2%) in *P. aeruginosa* (Strain 59-12-4-4) Infected Burned Rats.

| | MORTALITY | | | |
|---|---|---|---|---|
| | BURN (ONLY) CONTROL | INFECTION CONTROL | MAFENIDE ACETATE | MAFENIDE PHOSPHANILATE |
| DIED/ TOTAL | 2/78 | 78/81 | 22/82 | 8/101 |
| PERCENT | 2.5% | 96% | 26.8% | 7.9%** |

**$p < 0.01$ Mafenide Phosphanilate vs. Mafenide Acetate

As is clear from the comparison of mafenide phosphanilate and mafenide acetate activity levels in the experimental *Proteus mirabilis* burn wound infection the present compositions are much more potent than are those of the Mafenide acetate cream at a much lower dosage.

EXAMPLE II

The same procedures as in Example I were followed, excepting that the treatment agents were applied four hours after burning and inoculation and then once per day for 5 days. The results are present in Table II.

TABLE II

Therapeutic activities of Mafenide Acetate (11.2%) and Mafenide-phosphanilate (2%) in *P. Mirabilis* (strain 77-082234) infected burned rats.

| | BURN (ONLY) CONTROL | INFECTION CONTROL | MAFENIDE ACETATE | MAFENIDE PHOSPHANILATE |
|---|---|---|---|---|
| DIED/TOTAL | 0/34 | 34/35 | 24/34 | 2/34 |
| PERCENT | 0% | 97.1% | 70.5 | 5.8%** |

**P < 0.01 Mafenide Phosphanilate vs. Mafenide Acetate

The above results show significantly improved therapeutic activities at 2% mafenide phosphanilate as compared to mafenide acetate (11.2%), which is the commercial product.

Surprisingly, the presently claimed compounds extend the anti-microbial spectrum of mafenide and may reduce its toxicities of excess osmolality in carbonic anhydrase inhibitory activity from presently available mafenide compounds by reducing the concentration of mafenide required for effective antimicrobial activity. The mafenide phosphanilate compounds according to the present invention have a wide anti-microbial action including in vitro activity against strains of both gram(−) and gram(+) bacteria and some fungi. The studies indicated above show that in the *Pseudomonas aeruginosa* the mafenide phosphanilate compounds according to the present invention have greater than five times the therapeutic potency of mafenide acetate. Further, mafenide phosphanilate was found by the present inventors to be effective in the treatment of experimental *Proteus mirabilis* burn wound infections whereas the mafenide acetate salt is not effective.

The compounds according to the present invention show a synergistic anti-microbial effect for mafenide phosphanilate salts with especially high activity against *Pseudomonas aeruginosa*. This is particularly true in topical prophylaxis and therapy of burn wound infections.

Accordingly, the compounds according to the present invention are potent anti-microbial agents that unexpectedly increase the activity of the mafenide-phosphanilate as compared to the other mafenide salts and avoids or reduces the excess osmolality and carbonic anhydrase inhibitory activity to the subject when administered. This represents accomplishment of significant advancements in the art of treating microbial infections, particularly in burn victims. Such surprising results were not expected.

The above specific examples of the invention are not intended to limit the invention disclosed. Based upon the above disclosure and the above examples, other variations and permutations on the present invention will be apparent to one of ordinary skill in the art.

The foregoing description of the specific embodiments will so fully reveal the general nature of the invention that others can, by applying current knowledge, readily modify, and/or adapt for various applications such specific embodiments without departing from the generic concept and therefore such adaptations are intended to be comprehended within the meaning and range of equivalence of the disclosed embodiments. It is to be understood that the phraseology and terminology employed herein is for the purpose of description only and not a limitation.

We claim:

1. A compound of the formula I

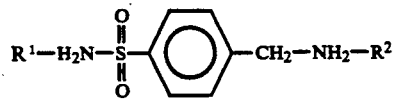

wherein $R^1$ and $R^2$ independently are absent or a phosphanilate group of formula II

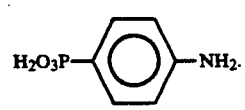

2. A compound according to claim 1, wherein $R^1$ and $R^2$ are each a phosphanilate group of formula II.

3. A compound according to claim 1, wherein $R^1$ is a phosphanilate group of formula II and $R^2$ is absent.

4. A compound according to claim 1, wherein $R^2$ is a phosphanilate group of formula II and $R^1$ is absent.

5. A pharmaceutical composition which comprises an anti-microbial effective amount of a compound according to claim 1 in association with a pharmaceutically acceptable diluent or carrier.

6. A composition according to claim 5 suitable for topical administration.

7. A composition according to claim 5, wherein $R^1$ and $R^2$ are each a phosphanilate group of formula II.

8. A composition according to claim 5, wherein $R^1$ is a phosphanilate group of formula II and $R^2$ is absent.

9. A composition according to claim 5, wherein $R^2$ is a phosphanilate group of formula II and $R^1$ is absent.

10. A method for treating or alleviating a microbial infection in a mammal which comprises administering to a mammal an anti-microbial effective amount of a compound of formula I according to claim 1.

11. A method according to claim 10, which comprises administering an effective amount of said compound of formula I wherein $R^1$ and $R^2$ are each a phosphanilate group of formula II.

12. A method according to claim 10, which comprises administering an effective amount of said compound of formula I wherein $R^1$ is a phosphanilate group of formula II and $R^2$ is absent.

13. A method according to claim 10, which comprises administering an effective amount of said compound of formula I, wherein $R^2$ is a phosphanilate group of formula II and $R^1$ is absent.

14. A method according to claim 10, wherein a microbe causing infection is selected from the group consisting of a Pseudomonas bacteria species or a Proteus bacteria species.

15. A method according to claim 14, wherein said microbial infection is of a burn wound.

16. A method according to claim 10, wherein the microbial infection is caused by either a gram(+) or a gram(−) bacteria.

* * * * *